United States Patent
Sriram et al.

(10) Patent No.: US 8,853,453 B2
(45) Date of Patent: *Oct. 7, 2014

(54) PROCESSES FOR REDUCING IMPURITIES IN LACOSAMIDE

(75) Inventors: Hari Mohan Sriram, Krishna (IN); Mukesh Kumar Madhra, Karnal (IN); Mukesh Kumar Sharma, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 79 days.

This patent is subject to a terminal disclaimer.

(21) Appl. No.: 13/574,833

(22) PCT Filed: Jan. 31, 2011

(86) PCT No.: PCT/IB2011/050425
§ 371 (c)(1),
(2), (4) Date: Oct. 11, 2012

(87) PCT Pub. No.: WO2011/092672
PCT Pub. Date: Aug. 4, 2011

(65) Prior Publication Data
US 2013/0204042 A1    Aug. 8, 2013

(30) Foreign Application Priority Data
Jan. 29, 2010 (IN) .............. 202/DEL/2010

(51) Int. Cl.
C07C 231/14 (2006.01)
C07C 227/18 (2006.01)
C07C 231/12 (2006.01)
C07C 231/02 (2006.01)
C07C 227/16 (2006.01)

(52) U.S. Cl.
CPC ............. *C07C 231/14* (2013.01); *C07C 227/18* (2013.01); *C07C 231/12* (2013.01); *C07C 231/02* (2013.01); *C07C 227/16* (2013.01)
USPC ............ 564/158; 564/138; 564/164; 564/165

(58) Field of Classification Search
CPC .................................................. C07C 231/14
USPC .................. 564/138, 164, 165, 158
See application file for complete search history.

(56) References Cited

U.S. PATENT DOCUMENTS

| RE38,551 E | 7/2004 | Kohn ............................. 514/616 |
| 8,440,861 B2 * | 5/2013 | Duran Lopez et al. ........ 564/158 |
| 2009/0143472 A1 | 6/2009 | Madhra et al. ................ 514/616 |

FOREIGN PATENT DOCUMENTS

| CN | 101591300 | 12/2009 | ........... C07D 237/22 |
| EP | 1 642 889 | 4/2006 | ........... C07C 275/16 |
| EP | 2 067 765 | 6/2009 | ........... C07C 237/06 |
| WO | WO 2006/037574 | 4/2006 | ........... C07C 275/16 |

OTHER PUBLICATIONS

*Novel intermediate compounds and their use in preparation of lacosamide*, published Mar. 25, 2009 on website IP.com as Prior Art Database Disclosure No. IPCOM000181080D.
Choi et al., "Synthesis and Anticonvulsant Activities of N-Benzyl-2-acetamidopropionamide Derivatives", *Journal of Medicinal Chemistry*, 39(9):1907-1916 (1996).
Morieux et al., "Synthesis and anticonvulsant activities of N-benzyl (2R)-2-acetamido-3-oxysubstituted propionamide derivatives", *Bioorganic & Medicinal Chemistry*, 16(19):8968-8975 (2008).

* cited by examiner

*Primary Examiner* — Shailendra Kumar

(57) ABSTRACT

The present invention relates to processes for reducing impurities in lacosamide during the preparation of lacosamide. The invention provides processes for minimizing or removing impurities such as (2R)-2-(acetylamino)-3-(benzylamino)-3-oxopropyl acetate of Formula II or (2R)-2-propanoylamino-N-benzyl-3-methoxypropionamide of Formula III in lacosamide.

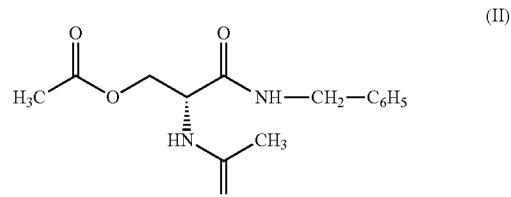

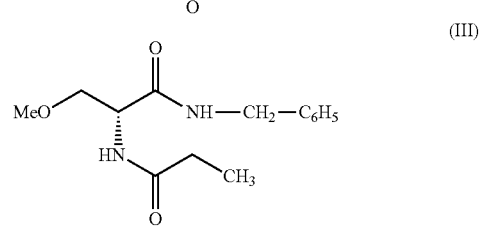

17 Claims, 1 Drawing Sheet

General Methods for Preparation of Lacosamide
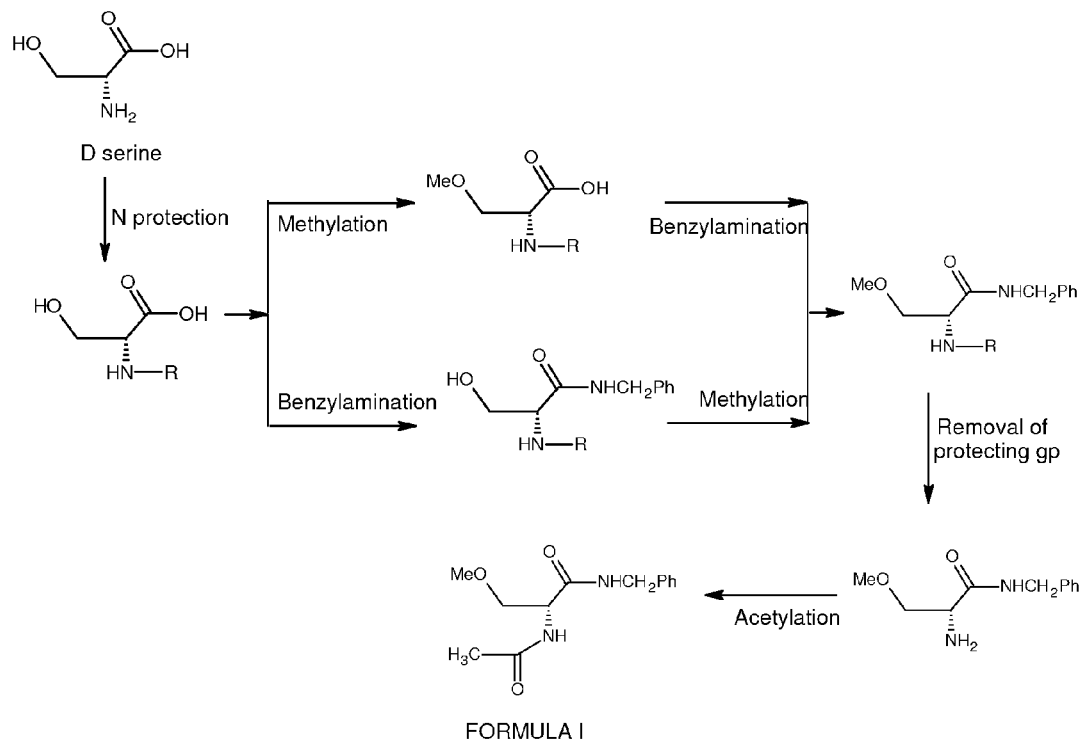
FORMULA I

PROCESSES FOR REDUCING IMPURITIES IN LACOSAMIDE

This application is a 371 of PCT/IB11/50425, filed Jan. 31, 2011.

FIELD OF THE INVENTION

The present invention relates to processes for reducing impurities in lacosamide during preparation of lacosamide. The invention provides processes for minimizing or removing impurities such as (2R)-2-(acetylamino)-3-(benzylamino)-3-oxopropyl acetate of Formula II or (2R)-2-propanoylamino-N-benzyl-3-methoxypropionamide of Formula III in lacosamide.

BACKGROUND OF THE INVENTION

Lacosamide (SPM 927, also referred to as harkoseride or ADD 234037), is chemically (R)-2-acetamido-N-benzyl-3-methoxypropionamide and represented by Formula I. It has been reported to be effective for the treatment of pain, epilepsy, fibromyalgia syndrome, osteoarthritis and migraine. It is also known to be useful for the treatment of CNS disorders in humans.

FORMULA I

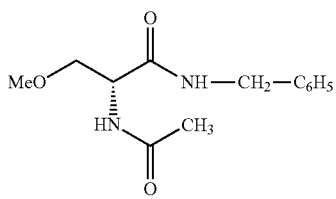

Lacosamide is available in the United States market as solution and tablet dosage forms with proprietary name of Vimpat®. The tablets are indicated as adjunctive therapy in the treatment of partial-onset seizures in patients with epilepsy aged 17 years and older. The solution (injection) dosage form is useful when oral administration is temporarily not feasible.

Lacosamide and its methods of preparation are disclosed in U.S. Reissue Pat. No. 38,551 (hereinafter referred to as the '551 patent). This provides three general methods for the preparation of lacosamide. The first two methods do not involve protection of active groups in intermediate compounds (such as amino, hydroxy and carboxylic acid groups). The third method involves protection of amino group present in D-serine with carbobenzoxy chloride (Cbz-Cl), subsequent O-methylation at hydroxy group followed by benzylamination at carboxylic (—COOH) group and finally removal of the 'Cbz' group followed by acetylation produces lacosamide.

An alternative method for the preparation of lacosamide is disclosed in WO 2006/037574 (hereinafter referred to as the '574 application) that comprises O-methylation of N-Boc-protected-D-serine ('Boc' refers to t-butoxycarbonyl) directly in one step by avoiding simultaneous formation of methyl ester moiety.

U.S. Publication No. 2009/0143472 (hereinafter referred to as U.S. '472 publication) and IP.com publication (IPCOM000181080D) describes processes for the preparation of lacosamide using trityl or pthalamide protected intermediates, respectively.

General methods known to date for the preparation of lacosamide can be represented by following synthetic scheme (FIG. 1, wherein R is nitrogen protecting group, e.g., Cbz, Boc, trityl, pthalamide etc.).

The inventors of the present invention observed that when protecting the amino group of D-serine, some percentage of hydroxyl groups (of D-serine) were also protected, thereby forming the protected or blocked intermediate compound(s). During the deprotection step (i.e., penultimate stage-FIG. 1), the blocked hydroxyl groups became deprotected and therefore in the last step, (2R)-2-(acetylamino)-3-(benzylamino)-3-oxopropyl acetate [hereinafter, referred as "Impurity-A"] of Formula II is obtained as an impurity along with lacosamide.

FORMULA II

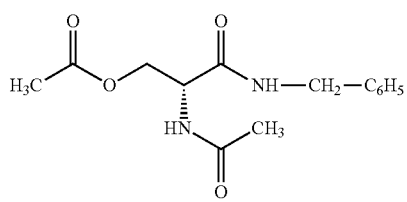

The present inventors also observed that commercially available acetic anhydride contained some percentage of propanoic anhydride. As a result, during the last acetylation step (figure I), (2R)-2-propanoylamino-N-benzyl-3-methoxypropionamide of Formula III (hereinafter referred as "Impurity-B") is obtained as an impurity along with lacosamide.

FORMULA III

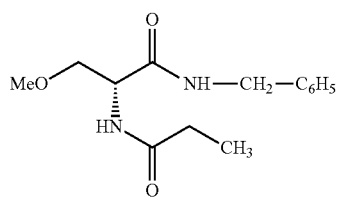

Therefore, lacosamide produced using known methods contains Impurity-A and/or Impurity-B. Thus, there is a need for simple and cost effective process for the preparation of lacosamide that eliminates or reduces the chances of having said impurities in lacosamide.

SUMMARY OF THE INVENTION

The present invention provides a process for reducing or eliminating the impurities in lacosamide.

The present invention provides a process for reducing the content of "Impurity-A" in lacosamide during the preparation of lacosamide, therein comprising a step for treating D-serine with the protecting reagent, wherein, number of moles for the protecting reagent are less then the number of moles of D-serine.

The present invention also provides a process for reducing the content of "Impurity-B" in lacosamide during the preparation of lacosamide, therein comprises a step of acetylating the compound of Formula IV in aqueous medium.

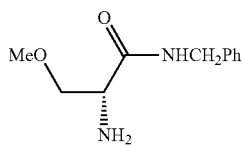

FORMULA IV

The present invention also provides lacosamide with an improved impurity profile.

The present invention also provides lacosamide substantially free of Impurity-A.

The present invention also provides lacosamide substantially free of Impurity-B.

The present invention also provides processes for preparation of lacosamide wherein lacosamide is substantially free of "Impurity-A" and "Impurity-B".

BRIEF DESCRIPTION OF THE FIGURE

FIG. 1: General methods for preparation of lacosamide.

DESCRIPTION OF TERMS

The term "lacosamide", as used herein, refers to R-enantiomeric form of 2-acetamido-N-benzyl-3-methoxypropionamide.

The term "O-methylation", as used herein, refers to attachment of methyl group to the main chain through an oxygen bridge. Alternatively the "O-methylation" is a process of converting —OH group into —OMe group in a given chemical compound.

The term "benzylamination", as used herein, refers to attaching —NH—CH$_2$—C$_6$H$_5$ group in a given compound in such a way that the terminal —NH moiety can form amide group.

The term "protecting reagent", as used herein, can be selected from the group comprising carbobenzyloxy chloride, tert.-butoxycarbonyl chloride, trityl chloride, pthaloyl chloride, and like reagents. Therefore, the protecting groups are carbobenzyloxy, tert.-butoxycarbonyl, trityl, pthaloyl, and the like.

The term "deprotection", as used herein, refers to removal of protecting group from the given compound.

The term "acetylation", as used herein, refers to the attachment of —COMe group to the N$^2$-amino group of a given compound. The term 'N$^2$-amino' refers to the amino group located at the second position in the main carbon chain of a given compound.

The term "trityl", as used herein, refers to triphenylmethyl group and "Me" refers to methyl group.

The term "alkoxy", as used herein, refers to —O-alkyl group, wherein the alkyl group is selected from the group having C$_1$-C$_6$ carbon atom such as methyl, ethyl, propyl, butyl, isobutyl, isopropyl, t-butyl, etc.

The term "Ph", as used herein, refers to phenyl group.

The term "about", as used herein, when used along with values assigned to certain measurements and parameters means a variation of 10% from such values, or in case of a range of values, means a 10% variation from both the lower and upper limits of such ranges.

The phrase "lacosamide with improved impurity profile", as used herein, is lacosamide wherein the Impurity-A is not detectable and Impurity-B is not more than 0.01% by HPLC. This also refers to the phrase "lacosamide substantially free of Impurity A and Impurity B".

The phrase "lacosamide substantially free of Impurity A", as used herein, is meant for lacosamide wherein the Impurity-A is not detectable by HPLC.

The phrase "lacosamide substantially free of Impurity B", as used herein, is meant for lacosamide wherein the impurity-B is not more than 0.01% by HPLC.

The term "ambient temperature", as used herein, refers to temperature of the surroundings wherein reaction is performed. Specifically "ambient temperature" is meant as temperature or range that lies in between about 20° C. to about 35° C.

DETAILED DESCRIPTION OF THE INVENTION

The present invention is described in detail in the following aspects.

The first aspect of the present invention provides a process for preparation of lacosamide comprising the following steps:

a) treating D-serine with a protecting reagent, wherein the number of moles of protecting reagent is less than the number of moles of D-serine, to obtain a compound of Formula V;

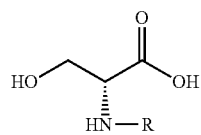

FORMULA V b) O-methylating the compound of Formula V obtained in step a) to produce a compound of Formula VI;

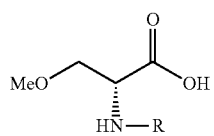

FORMULA VI c) benzylaminating the compound of Formula VI to produce a compound of Formula VII;

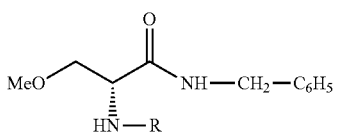

FORMULA VII d) deprotecting the compound of Formula VII to produce a compound of Formula IV; and

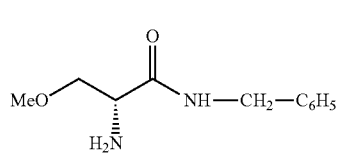

FORMULA IV e) acetylating the compound of Formula IV in aqueous medium, wherein R is the protecting group.

In an embodiment of this aspect of the invention, the lacosamide prepared is substantially free of Impurity-A.

In another embodiment of this aspect of the invention, the lacosamide prepared is substantially free of Impurity-B.

In another embodiment of this aspect of the invention, a process for the preparation of lacosamide with improved impurity profile is provided.

In another embodiment of this aspect, about 0.8 to about 0.9 moles of protecting reagent per mole of D-serine is used to prepare lacosamide.

The second aspect of the present invention provides a process for the preparation of lacosamide comprising the following steps:

a) treating D-serine with protecting reagent, wherein the number of moles of the protecting reagent is less then number of moles of D-serine, to obtain a compound of Formula V;

FORMULA V

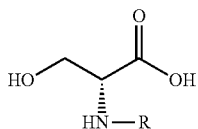

b) benzylaminating the compound of Formula V to produce a compound of Formula VIII;

FORMULA VIII

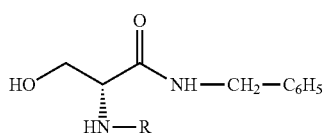

c) O-methylating the compound of Formula VIII to produce a compound of Formula VII;

FORMULA VII

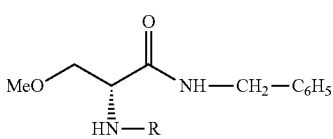

d) deprotecting compound of Formula VII to produce a compound of Formula IV; and

FORMULA IV

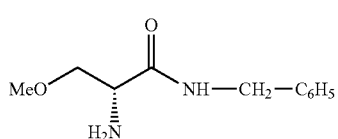

e) acetylating the compound of Formula IV in aqueous medium, wherein R is protecting group.

In an embodiment of this aspect of the invention, the lacosamide prepared is substantially free of Impurity-A.

In another embodiment of this aspect of the invention, the lacosamide prepared is substantially free of Impurity-B.

In another embodiment of this aspect of the invention, lacosamide with improved impurity profile is prepared.

In another embodiment of this aspect of the invention, about 0.8 moles to about 0.9 moles of the protecting reagent per mole of D-serine is used to prepare lacosamide.

The compound of Formula V of the present invention can be prepared by reacting D-serine with a protecting reagent wherein the number of moles of the protecting reagent is less than the number of moles of D-serine. Alternatively, the hydroxy and/or carboxylic group of D-serine can be protected by a silyl protecting group like trimethylsilyl, hexamethyldisilazane, etc., and then the free amino group in D-serine can be selectively protected using a protecting reagent wherein the number of moles of the protecting reagent is less than the number of moles of D-serine. Subsequently, the silyl protecting group can be removed by hydrolysis providing a high yield of the compound of Formula V.

The O-methylation method of the compound of Formula V or Formula VIII, the benzylamination method of compound of Formula V or Formula VI and the deprotection method of compound of Formula VII are described in detail in the U.S. '472 publication, the contents of which are incorporated herein by reference. These methods can also be implemented in the processes of preparation of lacosamide of the present invention. These methods can be applied for preparing lacosamide using any of the protecting reagents of the present invention.

The deprotected compound of Formula IV is then acetylated to provide lacosamide. Acetylation is performed in aqueous medium (i.e., comprises of water). For this purpose, acetic anhydride, acetyl chloride, acetic acid, or the like may be used as the acetylating agent. Acetylation can be performed optionally in the presence of a base. The base can be a nitrogen containing base, i.e., pyridine, dimethylaminopyridine, etc.

Accordingly, the base is added to the aqueous solution of compound of Formula IV and the acetylating agent is then slowly added to the mixture. The reaction is allowed to proceed for about 2 hour at temperature ranging from 5° C. to 40° C. The lacosamide prepared is then isolated from the reaction mixture and purified.

The present inventors preferably use acetic anhydride as acetylating agent and dimethylaminopyridine as base for the said acetylation purpose. Lacosamide so formed is purified with the help of suitable organic solvents such as dichloromethane, toluene, ethanol, ethyl acetate, etc.

A third aspect of the present invention provides a process for reducing the content of "Impurity-A" in lacosamide during preparation of lacosamide that preparation comprises a step of treating D-serine with the protecting reagent wherein number of moles of the protecting reagent is less then number of moles of D-serine.

In an embodiment of this aspect of the present invention, the lacosamide prepared is substantially free of Impurity-A.

In another embodiment of this aspect of the present invention, D-serine is treated with the protecting reagent wherein about 0.8 moles to about 0.9 moles of the protecting reagent per mole of D-serine is used.

D-serine is treated with the protecting reagent wherein number of moles of protecting reagent is less than number of moles of D-serine. Alternatively, the hydroxy and/or carboxylic group of the D-serine can be protected by silyl protecting group like trimethylsilyl, hexamethyldisilazane, etc., and then the free amino group in the D-serine can be selectively protected using protecting reagent wherein number of moles of protecting reagent is less than number of moles of D-serine. Subsequently, the silyl protecting group can be removed by hydrolysis reaction.

A fourth aspect of the present invention provides process for reducing content of "Impurity-B" in lacosamide during the preparation of lacosamide, such preparation comprises the step of acetylating the compound of Formula IV in aqueous medium.

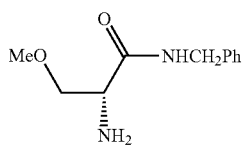

FORMULA IV

In an embodiment of this aspect of the present invention, the lacosamide prepared is substantially free of Impurity-B.

The compound of Formula IV is acetylated in aqueous medium (i.e., the medium comprises water) to provide lacosamide having reduced content of "Impurity-B". For this purpose, acetic anhydride, acetyl chloride, acetic acid, or the like may be used as the acetylating agent. Acetylation can be optionally performed in the presence a base. The base can be a nitrogen containing base, e.g., pyridine, dimethylaminopyridine etc.

Accordingly, base is added to the aqueous solution of compound of Formula IV and acetylating agent is then slowly added to the mixture. The reaction is allowed to proceed for about 2 hours at a temperature ranging from 5° C. to 40° C. The lacosamide prepared is then isolated from the reaction mixture and purified.

The present inventors preferably use acetic anhydride as the acetylating agent and dimethylaminopyridine as the base for the said acetylation. Lacosamide so formed is purified with the help of suitable organic solvents such as dichloromethane, toluene, ethanol, ethyl acetate, etc.

A fifth aspect of the present invention provides lacosamide with an improved impurity profile.

A sixth aspect of the present invention provides lacosamide substantially free of Impurity-A.

A seventh aspect of the present invention provides lacosamide substantially free of Impurity-B.

An eighth aspect of the present invention provides a composition comprising pharmaceutically effective amount of lacosamide with improved impurity profile and other pharmaceutically acceptable carrier, diluent and/or excipient.

While the present invention has been described in terms of its specific aspects, certain modifications and equivalents will be apparent to those skilled in the art and are intended to be included within the scope of the present invention.

In the following section aspects are described by way of example to illustrate the processes of the invention. However, this is not intended in any way to limit the scope of the present invention. Several variants of this example would be evident to persons ordinarily skilled in the art.

Example 1

Preparation of Lacosamide

Step 1: Preparation of N-trityl-D-serine

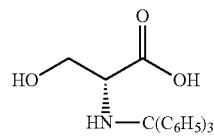

All operations until reaction quenching were carried out under anhydrous condition.

To the solution of D-Serine (100 g; 0.95 moles) in dichloromethane (1.0 L), trimethylsilyl chloride (361.79 g) was added in 15 minutes to 30 minutes. It was refluxed at 40° C. for 20 minutes and then cooled to ambient temperature. To the resultant solution, triethyl amine (433.27 g) dissolved in dichloromethane (200 ml) was added in 60 minutes to 90 minutes. It was refluxed at 40° C. to 45° C. for 2 hours and then cooled to 0° C. to −2° C. To the cooled solution, methanol (45.72 g) diluted with dichloromethane (200 ml) was added in 60 minutes to 75 minutes (exothermic reaction was observed). It was stirred for 15 minutes at 0° C. to 5° C. and then further raised to ambient temperature. At this temperature, triethyl amine (96.28 g) was added in 15 minutes to 20 minutes and stirred for 10 minutes. To the resultant reaction mixture, trityl chloride (238.78 g; 0.85 moles) was added in 6 lots at an interval of 10 minutes at ambient temperature and stirred for 3 hours. The reaction mixture was cooled to 5° C. and de-ionized water (500 ml) was added to it at 5° C. to 10° C. The reaction mixture was stirred for 15 minutes at the same temperature and allowed to settle for 15 minutes. The organic layer (dichloromethane layer) was separated and 5% citric acid monohydrate solution (500 ml) was added for 5 minutes to 10 minutes, stirred for 15 minutes at 5° C. to 10° C. and allowed to settle for 15 minutes. The organic layer (dichloromethane layer) was separated and de-ionized water (500 ml) was added at 5° C. to 10° C. for 10 minutes to 15 minutes, stirred for 15 minutes and allowed to settle. The organic layer obtained was separated and solvent was recovered at atmospheric pressure up to 45° C. Traces of solvent (if any) were recovered under vacuum at 35° C. to 40° C. To the remaining residue, toluene (100 ml) was added and heated to 50° C. under stirring for 15 minutes. The solvent was recovered under vacuum at 45° C. to 50° C. Toluene (250 ml) was again added to the residue at 50° C. and it was stirred for 15 minutes. This was cooled to ambient temperature and then hexanes (500 ml) were added. The mixture was stirred for 30 minutes and cooled further to 0° C. to 5° C. It was stirred at this temperature for 30 minutes. The solid obtained was filtered, washed with hexanes (200 ml) and suck dried. It was further dried in a vacuum tray dryer at 50° C. to 55° C. until moisture content was NMT 0.5%.

Dry weight: 290 g.

Step 2: Preparation of Lacosamide

Step 2A: In-Situ Preparation of O-Methyl-N-Trityl-D-Serine

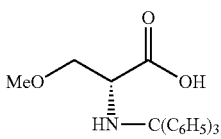

All the operations until reaction quenching are carried out under anhydrous condition.

To the stirred and cooled (at −15° C. to −10° C.) suspension of tetrahydrofuran (250 ml), imidazole (1.95 g) and sodium hydride (12.66 g), solid N-trityl-D-serine (50 g) was added in lots at an interval of 10 minutes. It was stirred for 45 minutes at −15° C. to −10° C. and then methyl iodide (40.85 g) was added to it at the same temperature (mild exothermic reaction was observed). The temperature of the reaction mass was raised to −5° C. to 0° C. and then it was stirred for 3 hours at the same temperature. De-ionized water (100 ml) was added to it and the reaction mass was cooled to 0° C. to 5° C. Acetic acid (9.8 ml) was added to the reaction mass and pH of the mass was adjusted to 6.5 to 7.0. Tetrahydrofuran was recovered completely under vacuum at 30° C. to 35° C. and dichloromethane (100 ml) and de-ionized water (100 ml) were added to the reaction mass at ambient temperature. This was stirred and allowed to settle for 15 minutes. The layers were separated. Dichloromethane (50 ml×2) was added to the aqueous layer, stirred, allowed to settle and layers were separated. The obtained organic layers were combined and de-ionized water (100 ml) was added to it. This was stirred, allowed to settle and then organic layer was separated. Anhydrous sodium sulphate (5 g) was added to the organic layer. It was stirred for 20 minutes and filtered through hyflo bed.

Step 2B: In-Situ Preparation of N-Benzyl-O-Methyl-$N^2$-Trityl-D-Serinamide

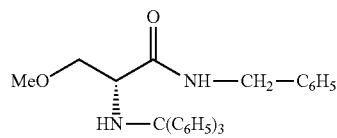

All the operations until reaction quenching are carried out under anhydrous condition.

Preparation of Solution A

The filtered organic layer (dichloromethane layer) obtained as above was cooled to 15° C. to 20° C. and N-methyl morpholine (NMM; 15.62 g) was added to it at 15° C. to 20° C. in 10 minutes to 15 minutes. The temperature of the solution was raised to 20° C. to 25° C. and it was stirred for 15 minutes at the same temperature.

Preparation of Solution B

Ethyl chloroformate (16.46 ml) was added to dichloromethane (104 ml) at ambient temperature. It was cooled to −10° C. to −15° C. and stirred for 15 minutes.

The Solution A was added to the Solution B in 60 minutes to 90 minutes at −15° C. to −10° C. and stirred for 30 minutes at the same temperature.

Preparation of Solution of Benzyl Amine

A solution of benzyl amine (18.38 g) in dichloromethane (52 ml) at ambient temperature was added to the above prepared solution in 60 minutes to 90 minutes at −15° C. to −10° C. and stirred for 60 minutes at −15° C. to 0° C. The obtained reaction mass was cooled to −10° C. to −15° C. and then N-methyl morpholine (NMM; 5.20 g) was added in minutes to 15 minutes. It was stirred for 15 minutes at the same temperature, and then ethyl chloroformate (5.48 g) was added and again stirred for 15 minutes. A solution of benzyl amine (6.12 g) in dichloromethane (26 ml) was slowly added at −15° C. to −10° C. The reaction mass, so obtained, was heated to 15° C. to 20° C. and stirred for 60 minutes at 20° C. to 25° C. De-ionized water (104 ml) was added to it, stirred and allowed to settle for minutes. The organic layer was separated and a precooled solution of citric acid (6 g in of 104 ml water) was added at 20° C. to 25° C. It was stirred, allowed to settle for 15 minutes and then organic layer was separated. To the organic layer, de-ionized water (104 ml) was added at 25° C. to 20° C., stirred, allowed to settle for 15 minutes and then organic layer was separated.

Step 2C: In-Situ Preparation of N-Benzyl-O-Methyl-D-Serinamide

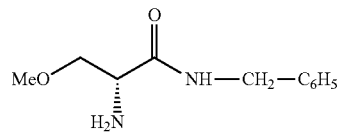

To the organic layer (the dichloromethane layer) as obtained above, concentrated hydrochloric acid (23.22 g dissolved in 65 ml de-ionized water) was added in 15 minutes to 20 minutes at 25° C. to 30° C. It was stirred for 60 minutes at the same temperature and allowed to settle for 15 minutes. The layers were separated. The organic and aqueous layers were separately collected. To the organic layer, de-ionized water (65 ml) was added, stirred and allowed to settle for 15 minutes. Again, the layers were separated and the organic and aqueous layers were separately collected. Both aqueous layers obtained were combined and dichloromethane (32.5 ml) was added at 25° C. to 30° C., stirred and allowed to settle for 15 minutes. The layers were separated and collected separately. From the aqueous layer, traces of dichloromethane were recovered under vacuum at 30° C. to 35° C. The aqueous layer was cooled to 25° C. to 30° C. and then filtered through a 0.45 micron filter. To the filtered layer, hexanes (65 ml) were added at ambient temperature, stirred and allowed to settle for 15 minutes. These layers were separated. The aqueous layer was again separated and cooled to 20° C. to 25° C. The pH of the aqueous layer was adjusted to 11 to 11.5 by using 10% sodium hydroxide solution (88 ml) at 20° C. to 25° C.

Step 2D: Preparation of Lacosamide

To the aqueous solution obtained as above, dimethyl amino pyridine (DMAP; 0.34 g) was added at ambient temperature. Acetic anhydride (14.68 g) was slowly added to the solution at 25° C. to 30° C. It was stirred for 2 hours at the same temperature and then 10% sodium hydroxide (120 ml) was added into it to adjust pH 6.5-7.5 at 25-30° C. Dichloromethane (325 ml) was added to it and the reaction mass was allowed to settle for 15 minutes. The layers were separately collected. To the aqueous layer, dichloromethane (260 ml) was added, stirred and allowed to settle for 15 minutes. The layers were separated. The organic layers were combined and washed with de-ionized water (65 ml). It was stirred for 10 minutes and allowed to settle for 15 minutes. The layers were separately collected. To the organic layer, activated carbon (1.5 g) was added at ambient temperature, stirred and then filtered through a hyflo bed at 25° C. to 30° C. The hyflo bed was washed with dichloromethane (30 ml) at 25° C. to 30° C. Solvent was recovered from the filtered and washed organic layer at atmospheric pressure and at 35° C. to 40° C. Traces of solvent, if any, were recovered under vacuum at 35° C. to 40° C. to get a solid. Ethyl acetate (30 ml) was added to the solid at 25° C. to 30° C. It was heated to 45° C. to 50° C. and stirred for 15 minutes. Solvent was recovered at atmospheric pressure and at 45° C. to 50° C. Ethyl acetate (210 ml) was again added at ambient temperature. It was stirred for 60 minutes at ambient temperature. The product obtained was filtered and suck dried for 60 minutes. Ethyl acetate (540 ml) was added to the wet product obtained and heated to reflux to obtain clear solution. The solution was stirred for 5 minutes at reflux temperature and then cooled to 30° C. in 1 hour. It was again stirred for 30 minutes at 25° C. to 30° C. and then cooled to 0° C. to 5° C. Toluene (90 ml) was added to it at the same temperature and stirred for 30 minutes. The solid obtained was filtered and washed with toluene (60 ml) at ambient temperature. The wet solid obtained was dried under vacuum at 60° C. to 65° C.

Dried weight: 17.5 g (loss on drying was 0.1%)
Impurity content of Formula II: Not detectable by HPLC
Impurity content of Formula III: 0.01% by HPLC
Impurity content of Formula II and/or Formula III in lacosamide were measured by HPLC (Agilent 1100 series) having photodiode array detectors. The analysis was performed at wavelength of 210 nm.

We claim:

1. A process for the preparation of lacosamide comprising the steps of:
    a) treating D-serine with a protecting reagent, wherein number of moles of the protecting reagent is less than the number of moles of D-serine, to obtain a compound of Formula V;

FORMULA V

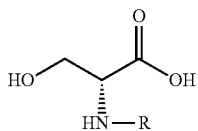

b) O-methylating the compound of Formula V obtained in step a) to produce a compound of Formula VI;

FORMULA VI

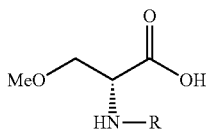

c) benzylaminating the compound of Formula VI to produce a compound of Formula VII;

FORMULA VII

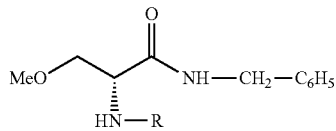

d) deprotecting the compound of Formula VII to produce a compound of Formula IV; and

FORMULA IV

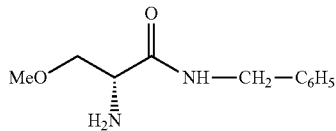

e) acetylating the compound of Formula IV in aqueous medium,
wherein R is a protecting group.

2. The process of claim 1 wherein the lacosamide prepared has levels of (2R)-2-(acetylamino)-3-(benzylamino)-3-oxopropyl acetate Impurity-A) that are undetectable by high performance liquid chromatography.

3. A process for the preparation of lacosamide comprising the steps of:
    a) treating D-serine with a protecting reagent, wherein number of moles of the protecting reagent is less than the number of moles of D-serine, to obtain a compound of Formula V;

FORMULA V

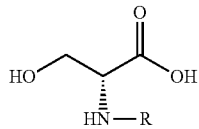

b) benzylaminating the compound of Formula V to produce a compound of Formula VIII;

FORMULA VIII

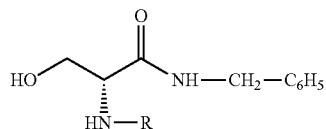

c) O-methylating the compound of Formula VIII to produce a compound of Formula VII;

FORMULA VII

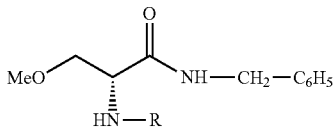

d) deprotecting compound of Formula VII to produce a compound of Formula IV; and

FORMULA IV

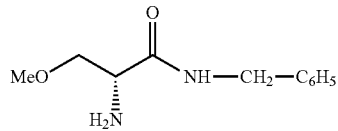

e) acetylating the compound of Formula IV in aqueous medium,
wherein R is protecting group.

4. The process of claim 3 wherein the lacosamide prepared has levels of (2R)-2-(acetylamino)-3-(benzylamino)-3-oxopropyl acetate (Impurity-A) that are undetectable by high performance liquid chromatography.

5. A process for reducing the content of (2R)-2-(acetylamino)-3-(benzylamino)-3-oxopropyl acetate ("Impurity-A") of Formula II in lacosamide during the preparation of lacosamide, the process comprising a step of treating D-serine with a protecting reagent wherein the number of moles of the protecting reagent is less than the number of moles of D-serine

FORMULA II

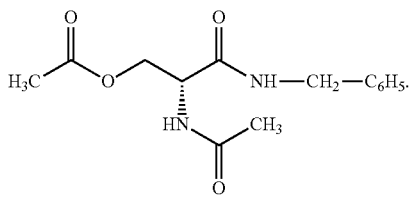

6. The process of claim 5 wherein the lacosamide prepared has levels of (2R)-2-(acetylamino)-3-(benzylamino)-3-oxopropyl acetate Impurity-A) that are undetectable by high performance liquid chromatography.

7. A process for reducing the content of (2R)-2-propanoylamino-N-benzyl-3-methoxypropionamide ("Impurity-B") of Formula III in lacosamide during the preparation of lacosamide, the process comprising a step of acetylating the compound of Formula IV in aqueous medium

FORMULA III

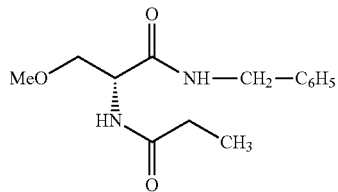

FORMULA IV

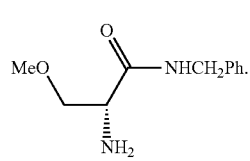

8. The process of claim 7 wherein lacosamide prepared has levels of (2R)-2-propanoylamino-N-benzyl-3-methoxypropionamide (Impurity-B) that are less than 0.01% as measured by high performance liquid chromatography.

9. The process of claim 1 wherein the lacosamide prepared has levels of (2R)-2-propanoylamino-N-benzyl-3-methoxypropionamide (Impurity-B) that are less than 0.01% as measured by high performance liquid chromatography.

10. The process of claim 3 wherein the lacosamide prepared has levels of (2R)-2-propanoylamino-N-benzyl-3-methoxypropionamide (Impurity-B) that are less than 0.01% as measured by high performance liquid chromatography.

11. The process of claim 1 wherein the protecting reagent comprises one or more of carbobenzyloxy chloride, tert.-butoxycarbonyl chloride, trityl chloride, and pthaloyl chloride.

12. The process of claim 3 wherein the protecting reagent comprises one or more of carbobenzyloxy chloride, tert.-butoxycarbonyl chloride, trityl chloride, and pthaloyl chloride.

13. The process of claim 5 wherein the protecting reagent comprises one or more of carbobenzyloxy chloride, tert.-butoxycarbonyl chloride, trityl chloride, and pthaloyl chloride.

14. The process of claim 1 wherein the protecting group comprises one or more of carbobenzyloxy, tert.-butoxycarbonyl, trityl, and pthaloyl.

15. The process of claim 3 wherein the protecting group comprises one or more of carbobenzyloxy, tert.-butoxycarbonyl, trityl, and pthaloyl.

16. The process of claim 5 wherein the protecting group comprises one or more of carbobenzyloxy, tert.-butoxycarbonyl, trityl, and pthaloyl.

17. The process of claim 1 wherein treating D-serine with a protecting reagent comprises treating the D-serine with about 0.8 to 0.9 moles of the protecting reagent per mole of D-serine.

* * * * *